(12) United States Patent
Meikle

(10) Patent No.: US 6,258,322 B1
(45) Date of Patent: Jul. 10, 2001

(54) SMEARER MECHANISM

(75) Inventor: Peter John Meikle, Surrey Hills (AU)

(73) Assignee: Vision Instruments, Inc., Mount Waverly (AU)

( * ) Notice: Subject to any disclaimer, the term of this patent is extended or adjusted under 35 U.S.C. 154(b) by 0 days.

(21) Appl. No.: 09/331,653

(22) PCT Filed: Dec. 23, 1997

(86) PCT No.: PCT/AU97/00879
   § 371 Date: Jun. 23, 1999
   § 102(e) Date: Jun. 23, 1999

(87) PCT Pub. No.: WO98/28603
   PCT Pub. Date: Jul. 2, 1998

(30) Foreign Application Priority Data

Dec. 24, 1996 (AU) .................................................. PO 4394

(51) Int. Cl.⁷ .......................... G01N 21/00; G01N 31/00; G01N 33/00; B01L 3/02; B05C 11/02
(52) U.S. Cl. ............................... 422/63; 422/65; 422/67; 422/100; 118/100
(58) Field of Search .............................. 422/100, 63, 65, 422/67; 436/46; 118/100, 120

(56) References Cited

U.S. PATENT DOCUMENTS

| | | | |
|---|---|---|---|
| 3,880,111 | * | 4/1975 | Levine et al. ............................... 118/4 |
| 4,061,108 | * | 12/1977 | Levine et al. ........................ 118/100 |
| 4,096,824 | * | 6/1978 | Levine et al. ........................ 118/100 |
| 4,151,915 | * | 5/1979 | Levine et al. ........................ 206/456 |
| 4,319,542 | * | 3/1982 | Ojima et al. ........................ 118/110 |
| 4,407,843 | * | 10/1983 | Sasaki et al. ............................. 427/2 |
| 5,443,790 | * | 8/1995 | Coeuveille et al. .................... 422/63 |
| 5,540,887 | * | 7/1996 | Yokota et al. ........................... 422/63 |
| 5,676,910 | * | 10/1997 | Levine et al. ........................... 422/65 |
| 5,766,549 | * | 6/1998 | Gao et al. ............................... 422/65 |
| 5,804,141 | * | 9/1998 | Chianese ................................. 422/63 |
| 6,110,320 | * | 8/2000 | Principe et al. .................... 156/273.3 |
| 6,110,425 | * | 8/2000 | Gao et al. ............................... 422/66 |

FOREIGN PATENT DOCUMENTS

| | | |
|---|---|---|
| 40904/96 | 7/1996 | (AU) . |
| 735 358 | 10/1996 | (EP) . |

OTHER PUBLICATIONS

Patent Abstracts of Japan, P–422, p. 154, JP 60–171431 A Sep. 4, 1985, T.ABE.
Patents Abstracts of Japan, P–169, p. 118, JP57–171260 A, Oct. 21, 1981, Isao Shindou.

* cited by examiner

*Primary Examiner*—Jill Warden
*Assistant Examiner*—Brian Gordon
(74) *Attorney, Agent, or Firm*—Shook, Hardy & Bacon L.L.P.

(57) ABSTRACT

Specimen preparation apparatus (10) for preparing a specimen smear on a microscope slide (28) includes a single drive shaft in the form of a horizontal screw (17). A smearer chuck assembly (15) threadably engages the screw whereby rotation of the screw causes, due to friction, rotation of the chuck assembly. Respective stop shafts (21, 22) limit the rotational movement of the chuck assembly and consequently when the assembly bears on one or the other of the stop shafts, continued rotation of the screw causes movement of the assembly axially along the screw. In this manner axial and limited rotational movement of the assembly in either direction is controlled by rotation of the screw in either direction and a smearer blade (19) mounted in the assembly may be moved between a smearing station (27), a rinsing station (30), a cleaning station (31) and a drying station (32). Rotation of the screw is controlled by a stepper motor (23) which is mounted on an end plate (12) of the apparatus for limited pivotal movement. A spring (24) restrains the pivotal movement and in combination with a degree of over rotation of the motor governs the amount of force applied by the smearer blade to the slide.

16 Claims, 8 Drawing Sheets

SMEARER MECHANISM

This application is the national phase of international application PCT/AU97/00879 filed Dec. 23, 1997 which designated the U.S.

BACKGROUND OF THE INVENTION

This invention relates to specimen preparation apparatus and more particularly to an apparatus for automatically smearing a blood sample on a microscope slide to create a blood film for subsequent examination.

The apparatus of this invention preferably forms part of a larger machine which automatically prepares a specimen sample (which may be blood or other types of specimens) from a tube containing the specimen. Such a machine is described, for example, in applicant's earlier Australian Patent Application No. PN 7621 and is fully automatic to the extent that it produces a completed stained slide sample ready for inspection by a Haematologist.

SUMMARY OF THE INVENTION

The object of this invention is to provide an improved apparatus for smearing blood or other specimen samples onto a microscope slide.

Accordingly one broad form of the invention provides specimen preparation apparatus for preparing a specimen smear on a microscope slide, said apparatus comprising a single horizontal drive shaft in the form of a longitudinal screw, a smearer chuck assembly threadably mounted on said shaft, and respective stop means for limiting rotational movement of said chuck assembly in opposite directions, rotation of said shaft causing limited rotational movement of said chuck assembly between said respective stop means and linear movement along said shaft, whereby a smearer blade in said chuck assembly may be caused to move between various operation stations by controlled rotation of said shaft.

BRIEF DESCRIPTION OF THE DRAWINGS

In order that the invention may be more readily understood one particular embodiment will now be described with reference to the accompanying drawings wherein.

DETAILED DESCRIPTION OF THE INVENTION

The blood smearing apparatus comprises a frame 10 which consists essentially of side plate 11, rear end plate 12 and front end plate 13. Whilst the orientation of the apparatus is quite arbitrary insofar as front, rear and sides are concerned, the orientation chosen for the description herein relates to the preferred orientation when the apparatus is installed in an automatic specimen preparation machine. In other words, the front end plate 13 is arranged towards the front of such a machine.

The frame 10 also includes a base 14 on which is mounted various components of the apparatus as will be described hereinbelow. A smearer chuck assembly 15 includes a head 16 which is mounted on horizontal screw 17 and threadably engages the screw 17 whereby rotation of the screw 17 causes the head 16 to move inwardly or outwardly, that is, between the end plates 12 and 13 according to the direction of rotation of the screw 17. The smearer chuck assembly 15 supports a smearer chuck 18 which holds a smearer blade 19 in a manner which allows easy change over of the smearer blade 19. A slide positioning arm 20 is also mounted on the head 16. Smearer chuck 18 can rotate about the longitudinal axis of screw 17 to allow smearer blade 19 to align to slide 28 during the smearing operation.

Figure 7:
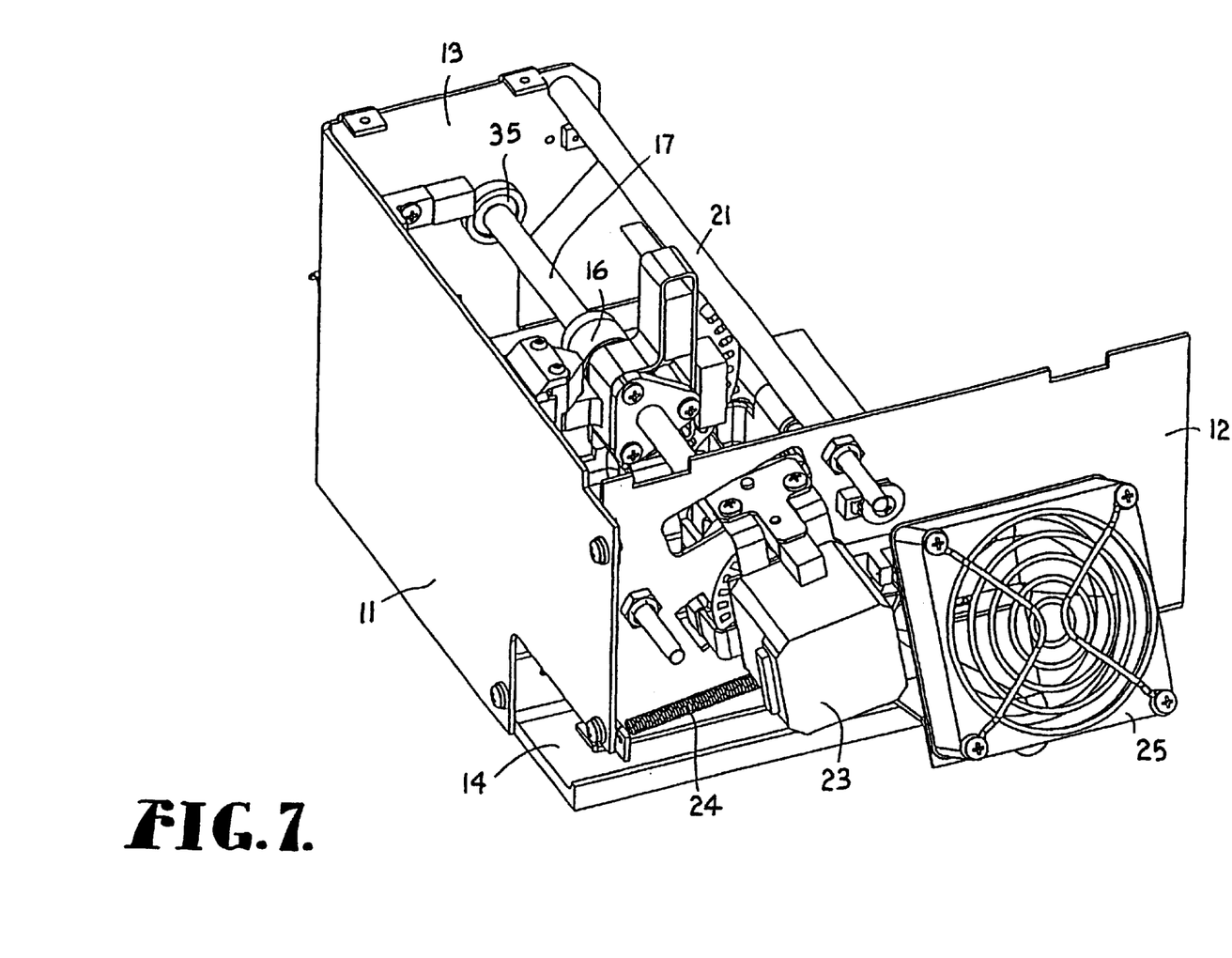
FIG. 7 is a perspective rear view of the apparatus of FIGS. 1–6.

A pair of spaced shafts 21 and 22 extend horizontally between the end plates 12 and 13 and provide stops against which the smearer chuck assembly 15 rests in one or other of its respective rotational positions. The horizontal screw 17 passes through rear end plate 12 where it is driven by electric stepper motor 23 (FIG. 7). The stepper motor 23 is pivotally mounted on rear end plate 12 and is capable of limited pivotal movement which is restrained by means of spring 24 (FIG. 7). Rotation of the horizontal screw 17 by means of stepper motor 23 initially causes the smearer chuck assembly 15 to rotate with the screw 17 due to frictional engagement between the two. The rotational movement of the assembly 15 is limited by one or other of the stop shafts 21 and 22 and once the assembly 15 engages a stop shaft, further rotational movement of the screw 17 causes the assembly 15 to move longitudinally along the screw 17 either inwardly or outwardly depending on the direction of rotation. In this manner, the position of the smearer blade 19 may be varied between a position wherein the blade is almost horizontal to a position wherein the blade is vertically oriented and furthermore the blade may be moved inwardly and outwardly and all these movements are controlled by the rotational direction provided by stepper motor 23.

A fan 25 is also mounted on the rear end plate 12 for the purpose of blowing drying air through slot 26 in the end plate 12 for purposes which will become apparent hereinbelow. A smearing station 27 is provided in the base 14 and a slide 28 may be transported into the smearing station 27 by means of carriage 29. The means by which the carriage 29 transports the slide 28 into the present apparatus does not constitute part of the present invention. A rinse station 30 is also provided on the base 14 and comprises a bath in which rinse solution flows over the smearer blade 19 to remove traces of the sample having been smeared. The rinse station 30 is displaced outwardly from the smearing station 27 towards the front end plate 13. Next to the rinse station 30 again in a direction outwardly towards the end plate 13, is a cleaning station 31 for the purpose of bleach cleaning the smearer at routine intervals during use of the machine. The cleaning station 31 contains bleaching solution for this purpose.

A drying station 32 is arranged on the base 14 beside the rinse station 30 and the cleaning station 31. In other words, the drying station is displaced sideways in the fore and aft direction of the apparatus and has a compliant cover 33 that allows the smearer chuck 18 and smearer blade 19 to enter the drying station and the compliant cover 33 prevents splatter of the rinse solution during the drying process to thereby prevents contamination of the apparatus or the previously completed smear sample. The drying station 32 is provided with an air stream by means (not shown) to blow dry the smearer blade 19 and prepare it quickly for the next smearing operation.

End bearings 34 and 35 are provided in the end plates 12 and 13 respectively for rotationally supporting the horizontal screw 17. The smearer chuck 18 has thumb screws 36 which enable easy removal and replacement of the smearer blade 19. The preceding description covers all the essential features of the apparatus according to this embodiment of the invention and the following description will describe the operation thereof.

Figure 2:
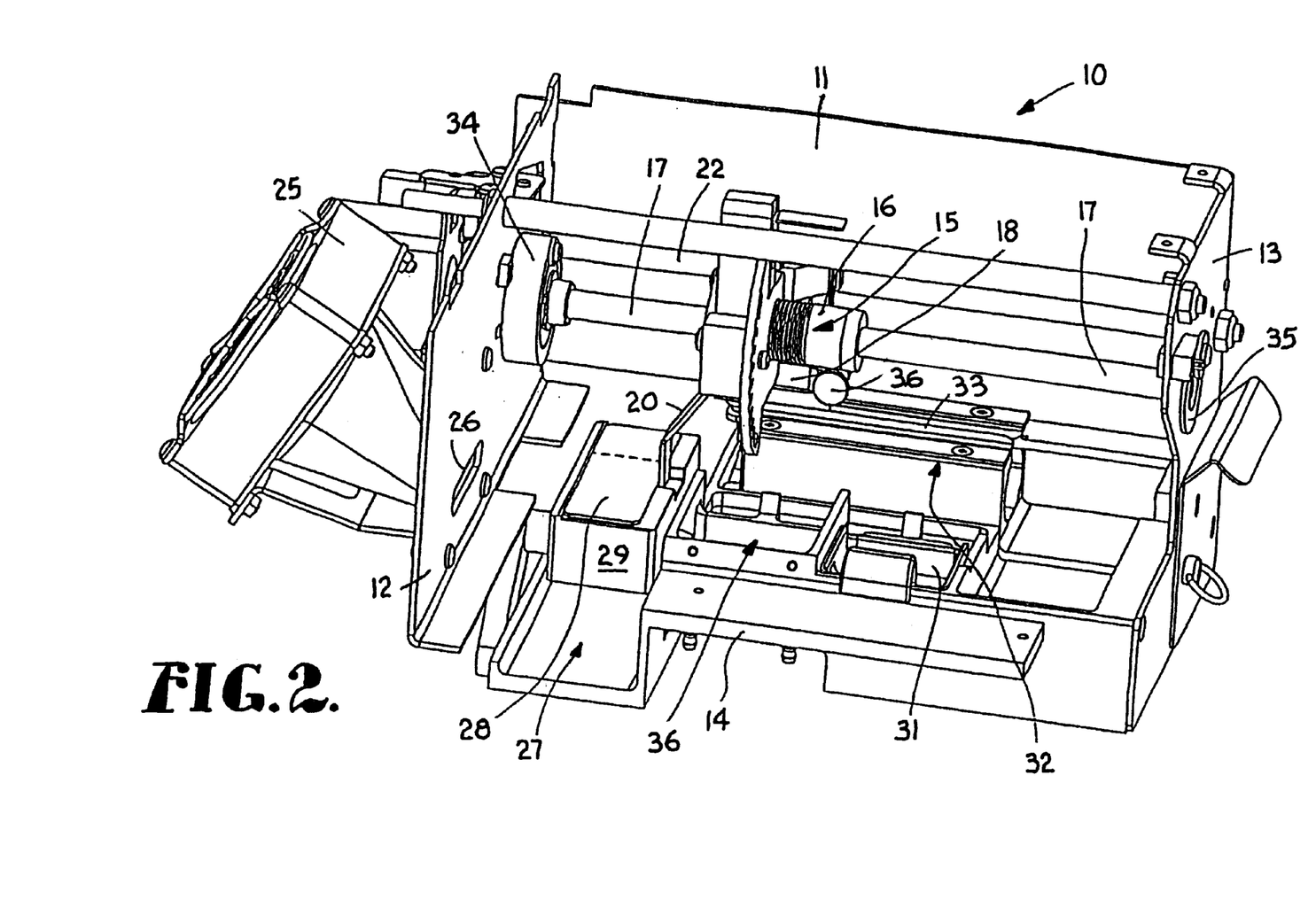
FIGS. 2–6 inclusive are similar views to FIG. 1 but show respectively, different positions of a smearer chuck assembly.
Figure 3:
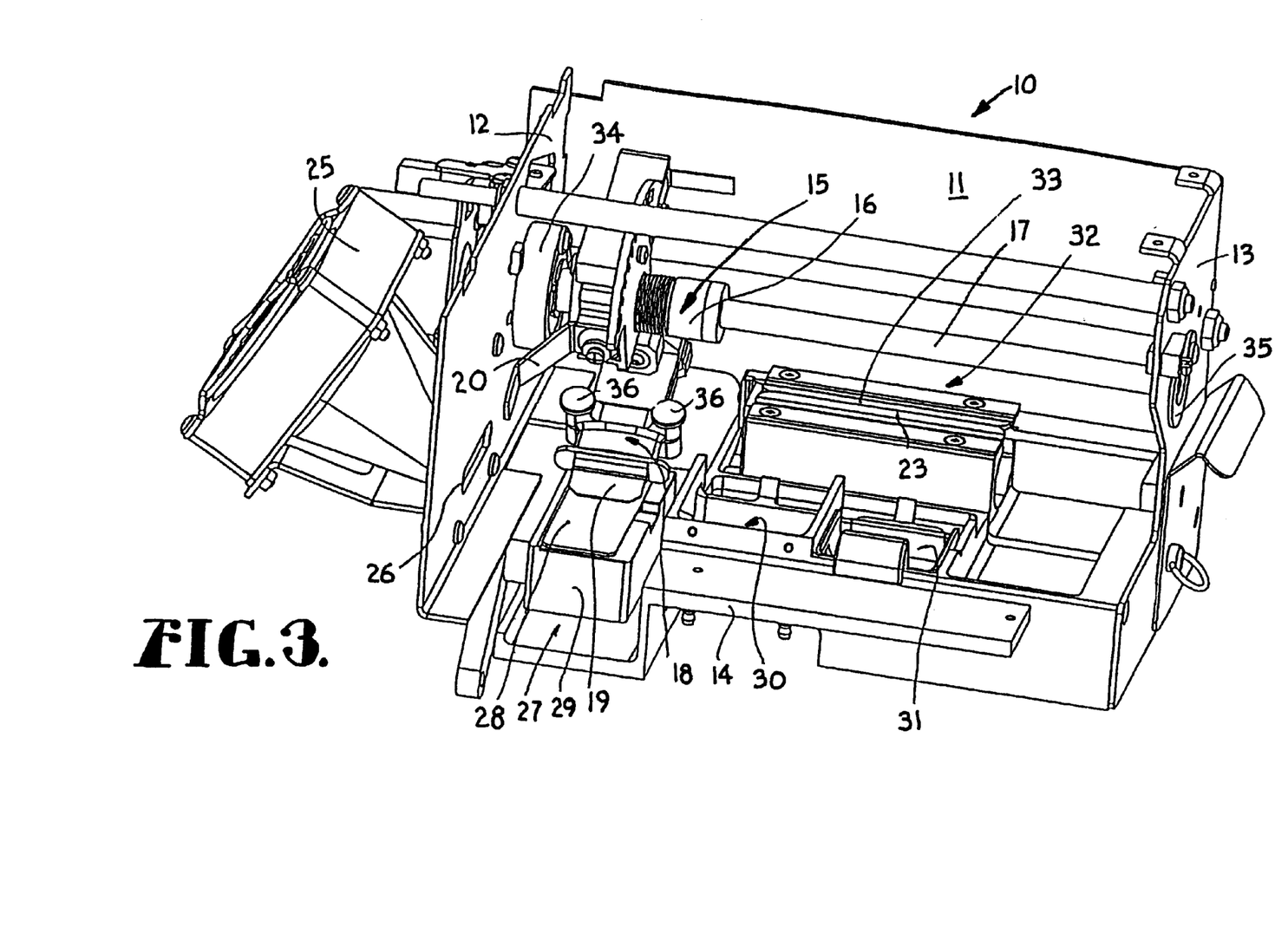
Figure 4:
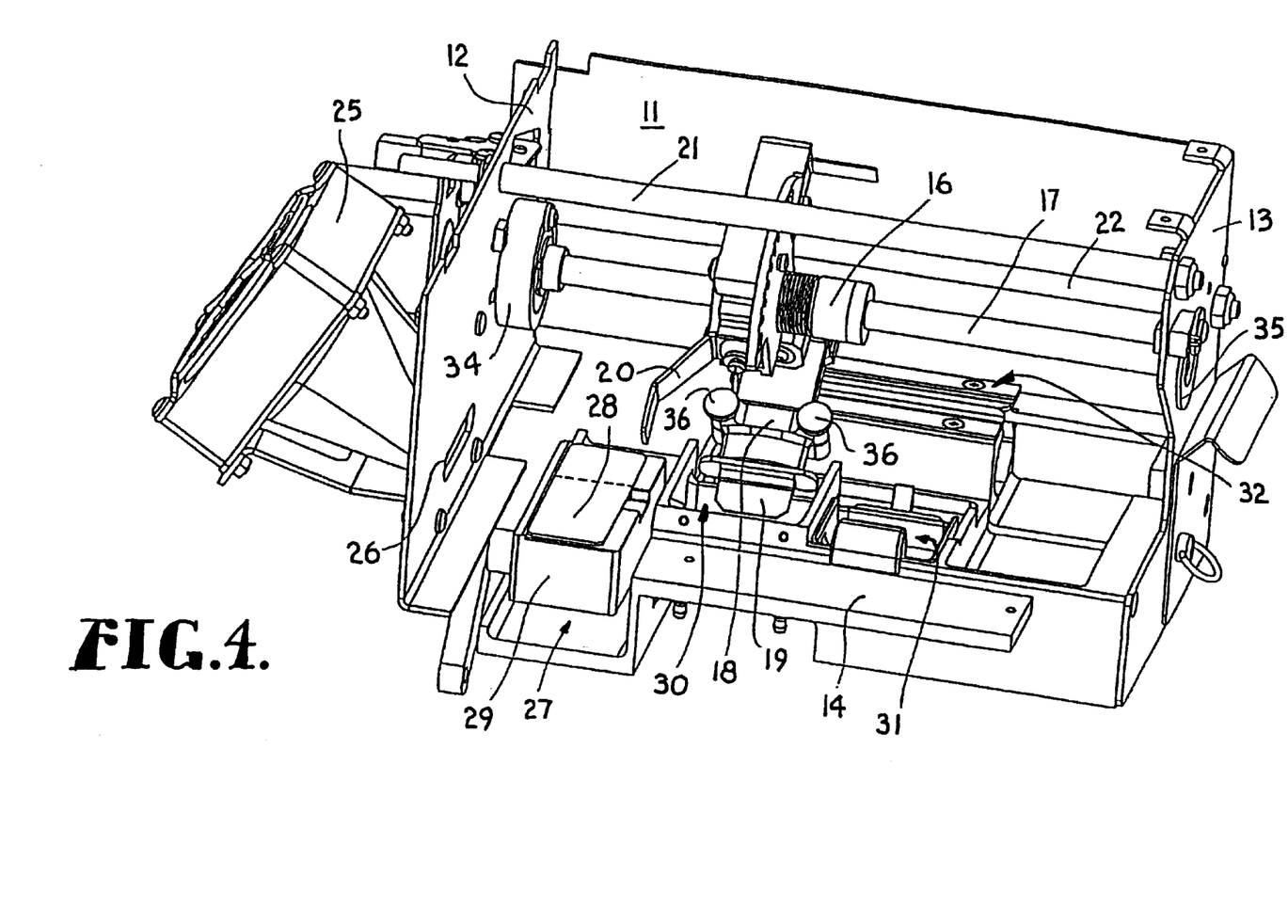
Figure 5:
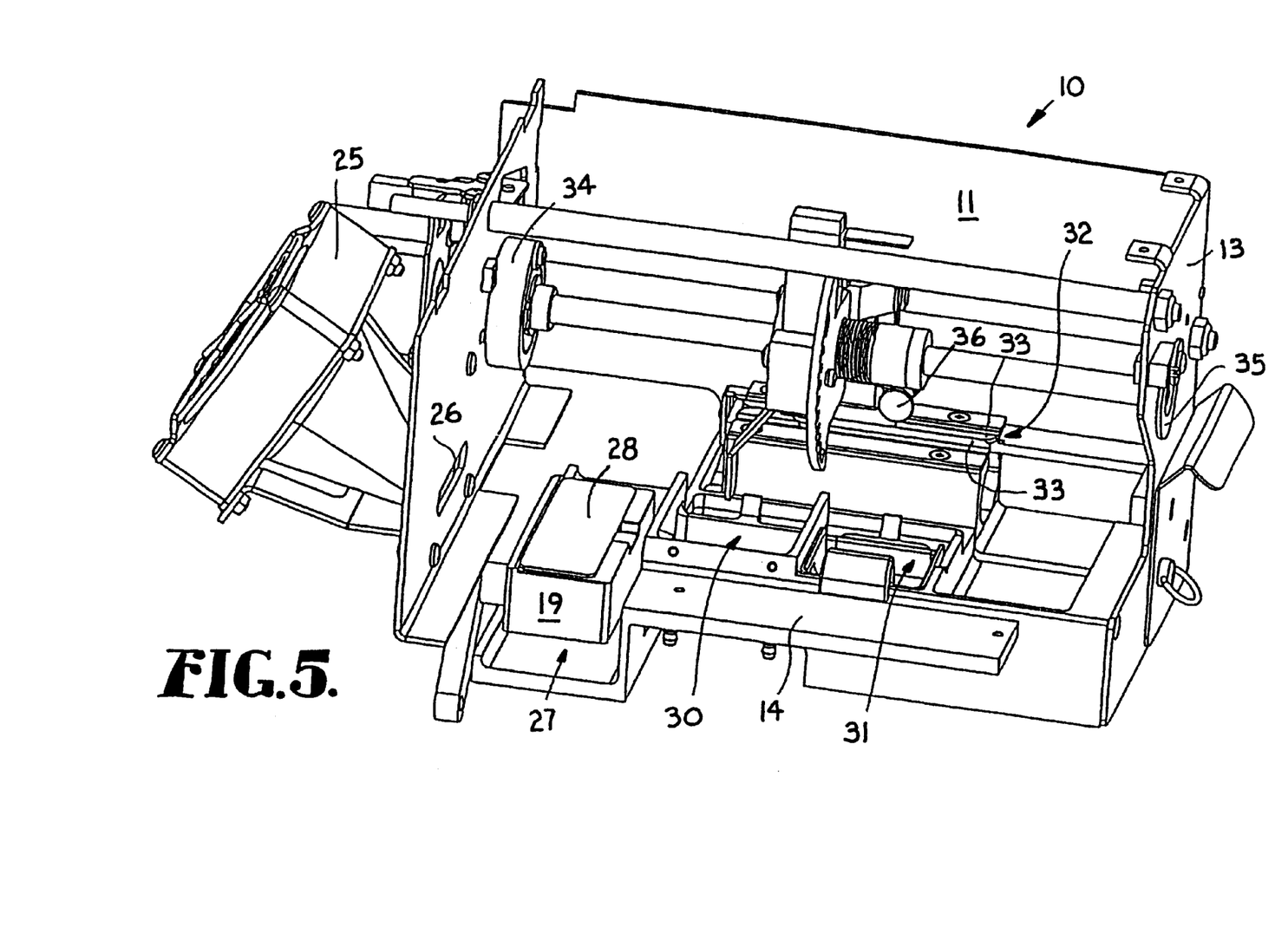
Figure 6:
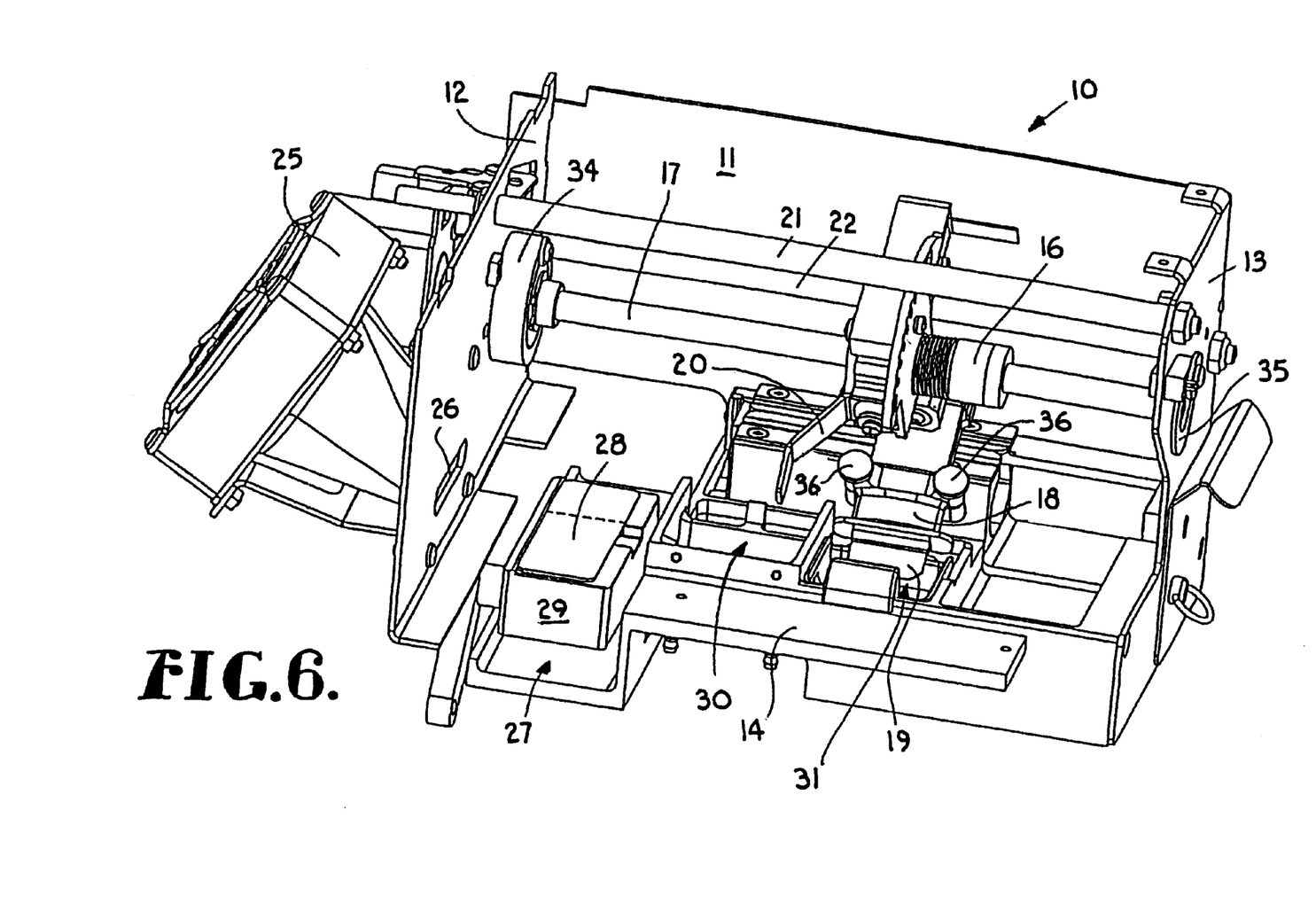
Figure 8A:
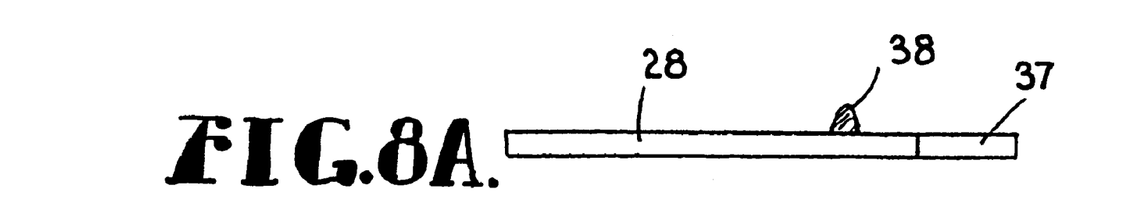
FIGS. 8A–8D are a series of schematic diagrams showing the combination of operations between smearer blade and microscope slide.

Commencing say, from the position of the apparatus shown in FIG. 5 where the smearer chuck 18 and smearer blade 19 are in the drying station 32, operation is as follows. The carriage 29 is moved to the right when viewed from the front, so that the slide 28 is in the correct position for receiving a sample of blood or other type of specimen. Counter-clockwise rotation of the screw 17 (when viewed from the front) causes the smearer chuck to remain in the vertical position and move inwardly towards the slide 28 until the slide positioning arm 20 has contacted and pushed the slide into position against one side of the carriage 29 (FIG. 2). The slide positioning arm 20 has compliance to allow for slide 28 width variation and to prevent stalling of the linear axis stepper motor 23. A sample of blood or other specimen is then dispensed onto the slide 28 by apparatus which is not shown or described herein as it does not constitute part of the present invention. The actual amount of blood is between 2–6 $\mu$L and 4 $\mu$L is the optimal amount. As shown in FIG. 8A) the blood is dispensed in a single drop 38 adjacent the label end 37 of the slide 28.

Figure 8B:
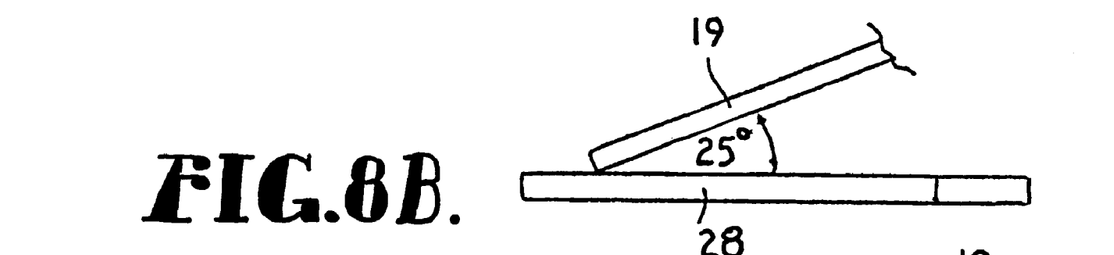

Once the blood or other sample is dispensed onto the slide 28 the screw 17 is rotated in the opposite direction which causes the chuck assembly 15 to move outwardly. Because the chuck 18 and blade 19 are still located within the drying station 13, it is not possible for the chuck assembly 15 to rotate from its vertical position. As soon as the positioning arm 20 is away from the carriage 29, the carriage with slide thereon is moved to the right (when viewed from the front) in the smearing station 27. The screw 17 is then rotated in the opposite direction causing the chuck assembly 15 to move inwardly to the inner stop position. Once the chuck 18 and blade 19 are clear of the drying station 32, the chuck assembly 15 rotates clockwise (when viewed from the front) causing the chuck and blade to move upwardly until the blade 19 is in a near horizontal orientation. The slide 28 is then moved back (in a left-hand direction) by means of the carriage 29 until it is in a position under the smearer chuck assembly 15. The smearer chuck 15 is then moved inwardly a small amount to cause it to rotate downwardly and bring the blade 19 into contact with the slide 28. The blade 19 makes an angle of about 25° with the slide 28 as shown in FIG. 8B. The motor is then caused to rotate a little further but since the blade cannot rotate because of its contact with the slide, the motor 23 is caused to rotate slightly on its mounting and thereby apply pressure between the blade 19 and the slide 28 due to the tension of spring 24. This spring tension increases the downward force with which the blade contacts the slide. The degree of over-rotation of motor 23 defines the contact force between the blade and slide which can therefore be software controlled. A contact force between 50 g–100 g is the required force between blade 19 and slide 28.

Figures 8C, 8D:
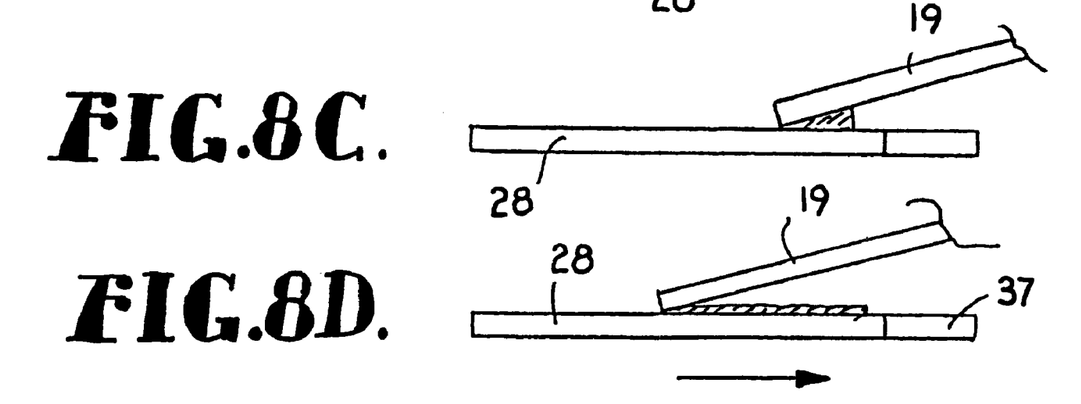

The smearer blade 19 is now sitting on top of the slide 28 and aligned to the slide with a controlled contact force as shown in FIG. 8B). The carriage 29 is then moved in a left-hand direction at between 150–300 mm/sec until the sample droplet (not shown) is in contact with the blade 19 as shown in FIG. 8C). After a pause of between 100–900 milliseconds to allow the sample to spread out along the contact edge of the blade 19, the carriage 29 is moved rapidly to the right (see FIG. 8D) causing the blade 19 to produce the sample smear on the slide 28 by drawing the blood along the slide by surface tension. The smear is then complete.

It will be apparent that either the blade 19 or the slide 28 may be moved as it is the relative movement which is important. In the present embodiment it is the slide 28 which is moved in the direction of the arrow in FIG. 8D) whilst the blade 19 remains stationery. The combination of the four important parameters of contact angle, contact force, wait time and relative velocity of movement between blade and slide produces a good quality smear irrespective of the haematocrit of the blood. There is only one programmable parameter, being the wait time, and this changes only the end shape of the smear. A longer wait time produces a squarer end on the blood smear whereas a shorter wait time causes the end of the smear to have rounded corners.

The next step is to rotate the screw 17 in a clockwise direction (when viewed from the front) causing the chuck assembly 15 to move outwardly which rotates it upwards and clear of the slide. The fan 25 provides an air stream over the smear to cause it to dry quickly. The slide 28 is then moved out of the apparatus by means of the carriage 29 to a next station in the machine of which the present apparatus forms part. Continued rotation of the screw 17 causes the chuck assembly 15 to continue its outward movement until the chuck 18 is over the rinse station 30.

Once over the rinse station 30, rotational movement of the screw 17 is reversed which causes the chuck assembly 15 to move inwardly thereby rotating the blade 19 downwardly and into the rinse station 30. Rinsing is then performed by causing rinse solution to flow over the smearer blade removing all traces of the sample.

Figure 1:
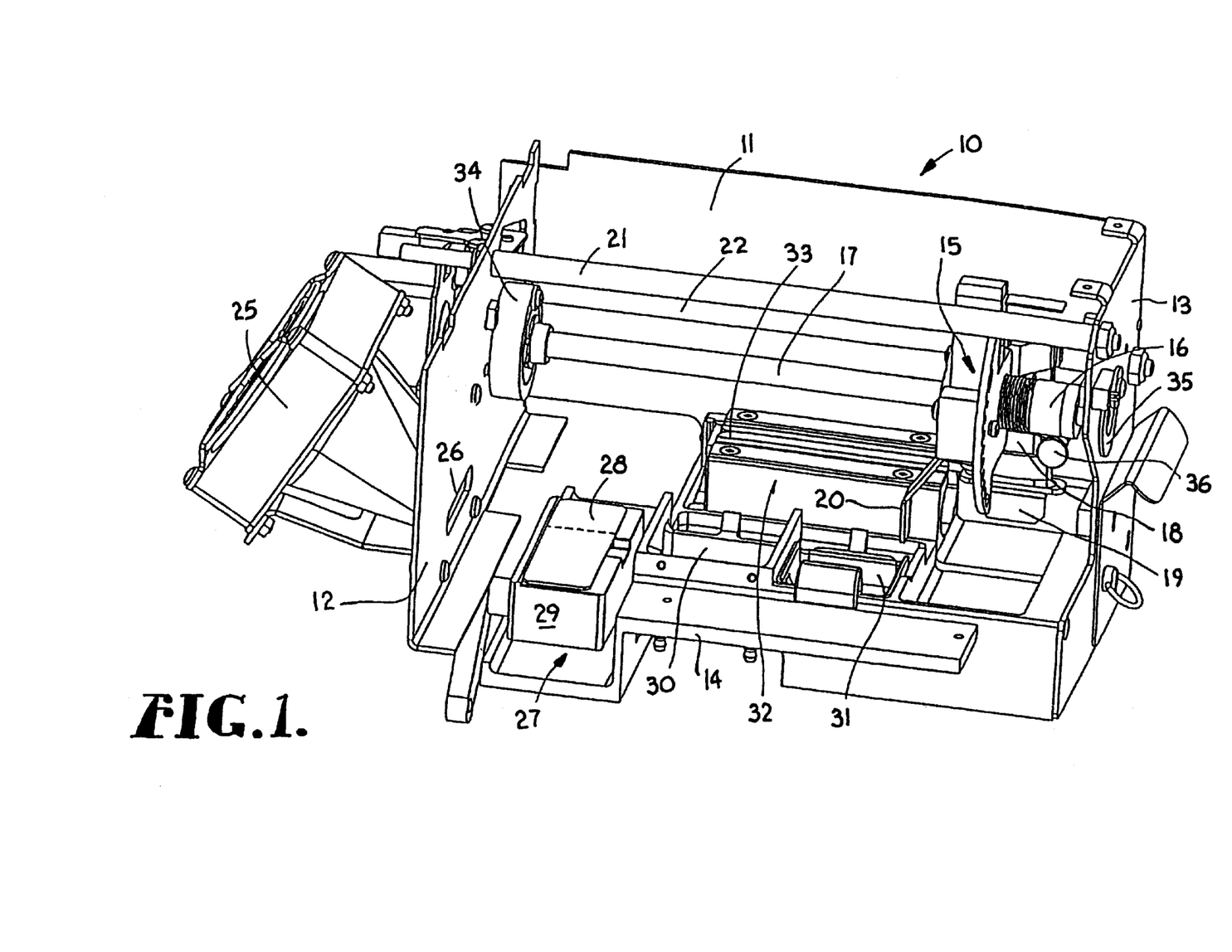
FIG. 1 is a perspective side view of a blood smearing apparatus according to the invention.

After completion of the rinsing, the chuck assembly 15 is moved outwardly by rotation of the screw 17 causing it pivot upwardly and continue moving until it is in a fully outward position. From this outward position, rotation of the screw 17 in the reverse direction initially causes the assembly 15 to rotate counter-clockwise (when viewed from the front) that is, downwardly to the position shown in FIG. 1. Continued rotation of the screw 17 in this direction causes the chuck assembly 15 to move inwardly until the chuck 18 and blade 19 are in the drying station 32. Once in the drying station, the screw 17 is rotated back and forth in opposite directions to move the smearer chuck and blade back and forth in an airstream within the drying station 32. This causes complete drying of the blade 19. The chuck and blade are then left in the drying station until the next cycle of operation is commenced.

When routine cleaning of the smearer blade 19 is required, the chuck assembly 15 is moved inwardly to the inner stop position. The assembly is then moved outward to rotate the smearer chuck assembly upwardly whereby the blade 19 is in a near horizontal position and has moved outwardly over the cleaning station 31. Rotation of the screw 17 is then reversed causing the chuck assembly to move inwardly which rotates the smearer blade 19 downwardly and into the cleaning station 32. The cleaning station 32 contains a bleaching agent to fully clean the blade 19. After waiting a sufficient time for proper cleaning, the screw 17 is rotated causing the assembly to move outwardly which rotates it upwards to the near horizontal position wherein it continues moving to the fully outward position. The smearer chuck assembly 15 is then moved inwardly to the inner stop position and then again moved outwardly to rotate it upward to the near horizontal position over the rinse station 30. Reverse rotation then causes the chuck 18 and blade 19 to rotate downwardly and into the rinse station wherein rinsing takes place. After rinsing the chuck assembly 15 is caused to rotate upwardly and move longitudinally in an outward direction by appropriate rotation of the screw 17 until the chuck assembly 15 is in the fully outward position. Reverse rotation of the screw 17 then causes the chuck assembly 15 to firstly rotate downwardly until the chuck 18 bears on the drying station 32 and the smearer blade 19 is oriented vertically. Further rotation of the screw 17 then causes the assembly to move inwardly to the drying station wherein the chuck 18 and blade 19 are moved back and forth as described previously in an airstream within the drying station 32 until the blade 19 is fully dried. The assembly is then left in this position with the blade 19 in the drying station until the next cycle of operation occurs. As should be apparent, the cleaning using a bleaching solution occurs only at routine intervals in the operation of the apparatus.

It should be apparent from the above that the apparatus of the present invention provides substantial improvements over prior art apparatus. By using a single motor to control longitudinal and rotational movement of the chuck assembly 15, there is a substantial reduction in manufacturing costs and a more compact apparatus. The construction is considerably simplified which makes use and maintenance of the apparatus far more convenient.

Since modifications within the spirit and scope of the invention may be readily effected by persons skilled in the art, it is to be understood that the invention is not limited to the particular embodiment described, by way of example, hereinabove.

What is claimed is:

1. A specimen preparation apparatus for preparing a specimen smear on a microscope slide, said apparatus comprising:
   a horizontal drive shaft;
   a smear chuck assembly comprising a smearer blade, said smear chuck assembly being threadably mounted on said drive shaft so as to be both rotatable in clockwise and counterclockwise directions and axially movable along said horizontal drive shaft;
   clockwise and counterclockwise stops that limit rotational movement of said smear chuck assembly in the clockwise and counterclockwise directions, respectively; and
   a plurality of operation stations.

2. The specimen preparation apparatus of claim 1, wherein said dive shaft comprises a longitudinal screw.

3. The specimen preparation apparatus of claim 1, wherein said operation stations comprise a smearing station, a rinsing station, and a drying station.

4. The specimen preparation apparatus of claim 1, wherein said stops comprise a set of stop shafts arranged parallel to said drive shaft, further wherein said smearer chuck assembly rotates with said drive shaft due to friction therebetween until said smearer chuck assembly engages one of said stop shafts.

5. The specimen preparation apparatus of claim 3, wherein said smearing station receives a movable carriage constructed and arranged to horizontally support a microscope slide, wherein said smear chuck assembly further comprises a slide positioning arm which, when said smear chuck assembly is axially moved to an outermost position at one end of said drive shaft, engages the slide and moves the slide on said carriage.

6. The specimen preparation apparatus of claim 5, wherein said operation stations further comprise a cleaning station for bleaching said smear blade at regular intervals.

7. The specimen preparation apparatus of claim 6, wherein said smearing chuck assembly further comprises a chuck and said drying station further comprises a compliant cover covering a drying chamber through which air is blown, and further wherein said compliant cover is constructed and arranged both to permit passage therethrough of said chuck and said smearer blade into said drying chamber for drying said chuck and said smearer blade with air and to prevent splattering of solution during drying.

8. The specimen preparation apparatus of claim 3, further comprising a stepper motor for controlling rotation of said horizontal drive.

9. The specimen preparation apparatus of claim 8, wherein said stops comprise a set of stop shafts arranged parallel to said drive shaft, further wherein said smearer chuck assembly rotates with said drive shaft due to friction until said smearer chuck assembly engages one of said stop shafts.

10. The specimen preparation apparatus of claim 9, wherein said smearing station receives a movable carriage constructed and arranged to horizontally support a microscope slide, wherein said smear chuck assembly further comprises a slide positioning arm which, when said smear chuck assembly is axially moved to an outermost position at one end of said drive shaft, engages the slide and moves the slide on said carriage.

11. The specimen preparation apparatus of claim 10, wherein said stepper motor is pivotally mounted on said apparatus and further comprises a tension spring that limits pivotal movement of said stepper motor, wherein, when said smearer blade is in contact with the slide, pivotal movement of said stepper motor urges said smearer blade further towards the slide.

12. The specimen preparation apparatus of claim 11, wherein said operation stations further comprise a cleaning station for bleaching said smear blade at regular intervals.

13. The specimen preparation apparatus of claim 12, wherein said chuck assembly further comprises a chuck and said drying station further comprises a compliant cover covering a drying chamber through which air is blown, and further wherein said compliant cover is constructed and arranged both to permit passage therethrough of said chuck and said smearer blade into said drying chamber for drying said chuck and said smearer blade with air and to prevent splattering of solution during drying.

14. The specimen preparation apparatus of claim 1, wherein said operation stations comprise a smearing station wherein a specimen smear is made on the microscope slide, wherein said apparatus is constructed and arranged to contact said smearer blade with the slide at an angle of about 25° with a contact force in a range of from 50 to 100 grams and, after an initial waiting period, to move the microscope slide relative to said smearer blade for a period of 100 to 900 milliseconds at 150 to 300 mm/sec.

15. The specimen preparation apparatus of claim 14, wherein said operation stations comprise a rinsing station and a drying station, and wherein said apparatus further comprising a stepper motor for controlling rotation of said horizontal drive.

16. The specimen preparation apparatus of claim 15, wherein said stops comprise a set of stop shafts arranged parallel to said drive shaft, further wherein said smearer chuck assembly rotates with said drive shaft due to friction until said smearer chuck assembly engages one of said stop shafts.

* * * * *

UNITED STATES PATENT AND TRADEMARK OFFICE
CERTIFICATE OF CORRECTION

PATENT NO. : 6,258,322 B1  Page 1 of 1
DATED : July 10, 2001
INVENTOR(S) : Peter John Meikle It is certified that error appears in the above-identified patent and that said Letters Patent is hereby corrected as shown below:

<u>Title page,</u>
Item [73], please correct the name and address of the Assignee to:

-- Vision Instruments Limited
Mount Waverley, Australia --

Signed and Sealed this

Eighth Day of April, 2003

JAMES E. ROGAN
*Director of the United States Patent and Trademark Office*